United States Patent
Katakura (10) Patent No.: US 9,110,302 B2
(45) Date of Patent: Aug. 18, 2015

(54) ENDOSCOPE OPTICAL SYSTEM

(71) Applicant: OLYMPUS MEDICAL SYSTEMS CORP., Tokyo (JP)

(72) Inventor: Masahiro Katakura, Tokyo (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 0 days.

(21) Appl. No.: 14/505,957

(22) Filed: Oct. 3, 2014

(65) Prior Publication Data

US 2015/0085376 A1    Mar. 26, 2015

Related U.S. Application Data

(63) Continuation of application No. PCT/JP2013/080993, filed on Nov. 18, 2013.

(30) Foreign Application Priority Data

Mar. 26, 2013 (JP) ................. 2013-064283

(51) Int. Cl.
    G02B 23/24    (2006.01)
    G02B 9/14     (2006.01)
    G02B 13/00    (2006.01)
    A61B 1/00     (2006.01)

(52) U.S. Cl.
    CPC ........ G02B 23/2438 (2013.01); A61B 1/00096 (2013.01); A61B 1/00188 (2013.01); G02B 13/0095 (2013.01); G02B 23/243 (2013.01)

(58) Field of Classification Search
    CPC ................... G02B 23/2438; G02B 23/243
    See application file for complete search history.

(56) References Cited

U.S. PATENT DOCUMENTS

| | | | |
|---|---|---|---|
| 4,312,572 | A | 1/1982 | Yamashita et al. |
| 2007/0206293 | A1 | 9/2007 | Takato |

(Continued)

FOREIGN PATENT DOCUMENTS

| | | |
|---|---|---|
| JP | 61-044283 | 10/1986 |
| JP | 05-100166 | 4/1993 |
| JP | 2007-233036 | 9/2007 |
| JP | 2010-032680 | 2/2010 |

(Continued)

OTHER PUBLICATIONS

International Search Report, dated Feb. 4, 2014, issued in corresponding International Application No. PCT/JP2013/080993.

*Primary Examiner* — David N Spector
(74) *Attorney, Agent, or Firm* — Kenyon & Kenyon LLP (57) ABSTRACT

An endoscope optical system has a first lens group having positive refractive power, an aperture diaphragm, a second lens group having negative refractive power and a third lens group having positive refractive group, the second lens group moving along an optical axis to perform focusing, the first lens group having a first lens having negative refractive power and a second lens having positive refractive power, and the optical system satisfying the following conditional equation:

$$-5.0 < H(76)*(1-nd01)/r2 < -0.2 \quad (1)$$

$$0.5 < (r1+r2)/(r1-r2) < 1.2 \quad (2)$$

where H(76) is a height at which a principal ray having an incidence angle of view of 76 degrees during normal observation passes through a surface on an image side of the first lens, nd01 is a refractive index of the first lens with respect to a line d, and r1 and r2 are respectively curvature radii of surfaces on the object side and the image side of the first lens.

11 Claims, 10 Drawing Sheets

(56) References Cited

U.S. PATENT DOCUMENTS

2010/0020408 A1 1/2010 Noguchi
2014/0233110 A1* 8/2014 Sone .......................... 359/738

FOREIGN PATENT DOCUMENTS

| JP | 2012-032576 | 2/2012 |
| JP | 2013-160901 | 8/2013 |

* cited by examiner

FIG. 10

ENDOSCOPE OPTICAL SYSTEM

CROSS-REFERENCE TO RELATED APPLICATIONS

This application is a Continuation Application of International Application PCT/JP2013/080993 filed on Nov. 18, 2013, which claims priority to Japanese Application No. 2013-064283 filed on Mar. 26, 2013.
The Contents of International Application PCT/JP2013/080993 and Japanese application No. 2013-064283 are hereby incorporated by reference herein in its entirety.

TECHNICAL FIELD

The present invention relates to an optical system having a focusing function, more particularly, to an endoscope optical system to be applied to an endoscope.

BACKGROUND ART

In recent years, in order to improve usability for operators and to improve accuracy in diagnostics, there have been proposed a variety of optical systems to be applied to medical endoscopes which performs focusing to provide observation in a wide range from high-magnification observation at close range to far distance observation by.
As examples of such endoscope optical systems, PTL 1 to PTL 4 disclose optical systems which are all composed of three groups of positive, negative and positive groups and in which focusing is performed by the second group moving along an optical axis.

CITATION LIST

Patent Literature

{PTL 1}
Japanese Unexamined Patent Application, Publication No. 2010-32680
{PTL 2}
Japanese Unexamined Patent Application, Publication No. Hei 5-100166
{PTL 3}
Japanese Unexamined Patent Application, Publication No. 2007-233036
{PTL 4}
Japanese Unexamined Patent Application, Publication No. 2012-32576

SUMMARY OF INVENTION

Technical Problem

However, because the optical systems disclosed in PTL 1 to PTL 4 all have a narrow angle of view of approximately 135 degrees at a maximum, these optical systems are not suitable for observation of a site which requires a wide angle of view, for example, a back side of folds of large intestine when the optical systems are applied to lower endoscopes. Meanwhile, in order to widen the angle of view, it is necessary to reduce a curvature and increase negative refractive power of the first negative lens group, or dispose the second negative lens. If the negative refractive power is increased, however, aberration, particularly, off-axis aberration may occur, and if the second negative lens is disposed, a diameter of the lens may become large.

The present invention has been made in view of the above-described circumstances, and an object of the present invention is to provide a smaller size endoscope optical system which has a wide angle of view with appropriately corrected aberration.

Solution to Problem

To achieve the above-described object, the present invention provides the following solution.
One aspect of the present invention is an endoscope optical system including a first lens group having positive refractive power, an aperture diaphragm, a second lens group having negative refractive power and a third lens group having positive refractive power, in this order from an object side toward an image side, focusing being performed by the second lens group moving along an optical axis, the first lens group including a first lens having negative refractive power and a second lens having positive refractive power, in this order from the object side, and the endoscope optical system satisfying the following conditional equations:

$$-5.0 < H(76)*(1-nd01)/r2 < -0.2 \quad (1)$$

$$0.5 < (r1+r2)/(r1-r2) < 1.2 \quad (2)$$

where $H(76)$ is a height at which a principal ray having an incidence angle of view of 76 degrees during normal observation passes through a surface on the image side of the first lens, $nd01$ is a refractive index of the first lens with respect to a line d, and $r1$ and $r2$ are respectively curvature radii of a surface on the object side and the surface on the image side of the first lens.

BRIEF DESCRIPTION OF DRAWINGS

FIGS. 2A and 2B are cross-sectional diagrams illustrating an overall configuration of an endoscope optical system according to Example 1 of the present invention.
FIG. 2A illustrates a normal observation state and FIG. 2B illustrates a high-magnification observation state;
FIGS. 5A and 5B are cross-sectional diagrams illustrating an overall configuration of an endoscope optical system according to Example 2 of the present invention.
FIG. 5A illustrates a normal observation state,
and FIG. 5B illustrates a high-magnification observation state;
FIGS. 8A and 8B are cross-sectional diagrams illustrating an overall configuration of an endoscope optical system according to Example 3 of the present invention.
FIG. 8A illustrates a normal observation state,
and FIG. 8B illustrates a high-magnification observation state.

DESCRIPTION OF EMBODIMENT

An endoscope optical system according to one embodiment of the present invention will be described below with reference to the drawings.

Figure 1:
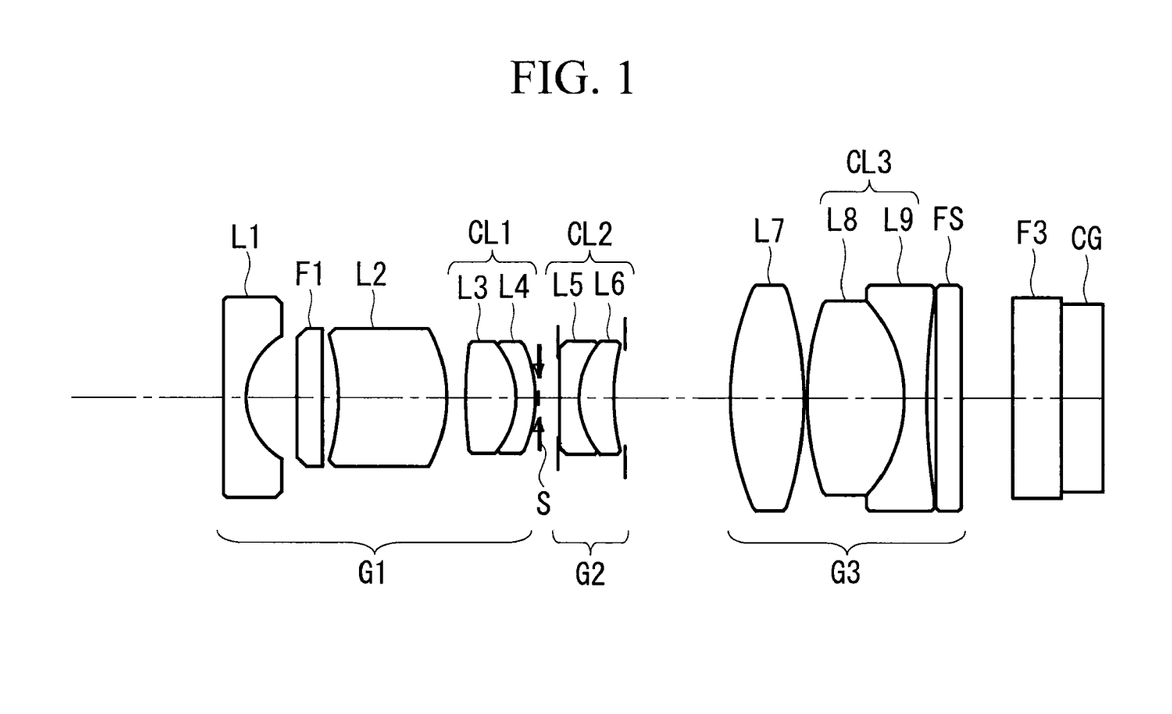
FIG. 1 is a cross-sectional diagram illustrating an overall configuration of an endoscope optical system according to one embodiment of the present invention.

FIG. 1 is a cross-sectional diagram illustrating an overall configuration of the endoscope optical system according to this embodiment. As illustrated in FIG. 1, the endoscope optical system includes a first positive lens group G1, an aperture diaphragm S, a second negative lens group G2 and a third positive lens group G3, in this order from an object side toward an image side.

The first positive lens group G1 has a first negative lens L1, a parallel flat plate F1, a second positive lens L2, a third positive lens L3 and a fourth negative lens L4, in this order from the object side toward the image side. Among these, the third positive lens L3 and the fourth negative lens L4 are connected to form a connected lens CL1.

The second negative lens group G2 has a connected lens CL2 in which a fifth negative lens L5 and a sixth positive lens L6 are connected in this order from the object side.

The third positive lens group G3 has a seventh positive lens L7, an eighth positive lens L8, a ninth negative lens L9 and a parallel flat plate F2, in this order from the object side. Among these, the eighth positive lens L8 and the ninth negative lens L9 are connected to form a connected lens CL3.

Imaging elements which are not illustrated are disposed near an image surface of the endoscope optical system to form an endoscope optical system and an imaging optical system. To the imaging elements, a parallel flat plate F3 and a cover glass CG for protecting an imaging surface are pasted.

Here, the endoscope optical system is configured to satisfy the following conditional equations (1) and (2):

$$-5.0 < H(76) * (1 - nd01)/r2 < -0.2 \tag{1}$$

$$0.5 < (r1 + r2)/(r1 - r2) < 1.2 \tag{2}$$

where H(76) is a height at which a principal ray having an incidence angle of view of 76 degrees during normal observation passes through a surface of the first lens L1 on the image side, nd01 is a refractive index of the first lens L1 with respect to a line d, and r1 and r2 are respectively curvature radii of a surface on the object side and the surface on the image side of the first lens L1.

The conditional equation (1) relates to the height at which the principal ray is incident on the first lens L1, the refractive index and the curvature of the principal ray which is incident on a surface of the first lens L1 at an incidence angle of 76 degrees. The conditional equation (1) is an equation for defining an amount corresponding to angular variation of a ray before and after the ray is refracted on the surface of the first lens, which is part of an invariant of Abbe, that is, a refraction amount. It is undesirable that the value exceeds an upper limit of the conditional equation (1), because the refraction amount is too large, which may increase a possibility of causing off-axis aberration. It is also undesirable that the value is below a lower limit of the conditional equation (1), because the refraction amount is too small, which may extremely increase the diameters of the lenses.

The conditional equation (2) relates to a shape factor of the first lens L1 of the negative lens group. If the value falls within the range of the conditional equation (2), it is possible to obtain necessary negative refractive power while maintaining a wide angle of view. It is undesirable that the value is below a lower limit of the conditional equation (2), because the refractive power of the first negative lens L1 decreases. It is also undesirable that the value exceeds an upper limit of the conditional equation (2), because productivity of the lens significantly decreases.

By employing a configuration having the first positive lens group G1, the aperture diaphragm S, the second negative lens group G2 and the third positive lens group G3, it is possible to reduce the number of lenses constituting each group while maintaining a wide angle of view and enabling focusing, so that it is possible to reduce the entire length and reduce cost.

It is more preferable that the endoscope optical system satisfies the following conditional equations (1)' and (2)' or conditional equations (1)" and (2)" in place of the above-described conditional equations (1) and (2):

$$-1.0 < H(76) * (1 - nd01)/r2 < -0.5 \tag{1}'$$

$$0.7 < (r1 + r2)/(r1 - r2) < 1.1 \tag{2}'$$

$$-0.85 < H(76) * (1 - nd01)/r2 < -0.60 \tag{1}''$$

$$0.97 < (r1 + r2)/(r1 - r2) < 1.03 \tag{2}''$$

Further, it is more preferable that the endoscope optical system 1 satisfies the following conditional equations (3) to (12).

$$0.5 < D\_L02/ih < 5.0 \tag{3}$$

where $D\_L02$ is a thickness of the second lens L2 on the optical axis, and ih is a maximum image height.

The conditional equation (3) relates to the thickness of the second positive lens L2 on the optical axis. If the thickness defined in the conditional equation (3) is appropriate, it is possible to make the entire length appropriate while favorably correcting off-axis aberration such as astigmatism. It is undesirable that the value exceeds an upper limit of the conditional equation (3), because the entire length becomes too long. It is also undesirable that the value is below a lower limit of conditional equation (3), because off-axis aberration such as astigmatism is likely to occur.

It is more preferable that the endoscope optical system satisfies the following conditional equation (3)' or conditional equation (3)" in place of the above-described conditional equation (3):

$$0.9 < D\_L02/ih < 3.0 \tag{3}'$$

$$1.4 < D\_L02/ih < 1.7 \tag{3}''$$

$$1.65 < nd01 < 2.4 \tag{4}$$

where nd01 is a refractive index of the first lens with respect to a line d.

The conditional equation (4) relates to the refractive index of the first negative lens, and if the refractive index falls within the range of the conditional equation (4), because the first lens has an appropriate refractive index, even if the curvature of the first negative lens is not extremely large, it is possible to obtain appropriate negative refractive power. It is undesirable that the refractive index is below a lower limit of the conditional equation (4), because the first negative lens L1 is required to have an extremely large curvature, which may increase possibility of causing off-axis aberration. It is also undesirable that the refractive index exceeds an upper limit of the conditional equation (4), because it makes significantly difficult to get a lens itself, and it increases the cost.

It is more preferable that the endoscope optical system satisfies the following conditional equation (4)' or conditional equation (4)" in place of the above-described conditional equation (4):

$$1.75 < nd01 < 2.0 \quad (4)'$$

$$1.85 < nd01 < 1.9 \quad (4)''$$

$$10 < v41 - v42 < 45 \quad (5)$$

where $v41$ and $v42$ are respectively Abbe's numbers of a lens having negative refractive power and a lens having positive refractive power of the second lens group.

The conditional equation (5) relates to a connected lens CL2 of the second lens group G2, and if a difference between the Abbe's numbers falls within the conditional equation (5), because the difference between the Abbe's numbers is appropriate, even if the second lens group G2 is driven during focusing, extreme chromatic aberration does not occur. It is undesirable that the difference between the Abbe's numbers exceeds an upper limit or a lower limit of the conditional equation (5), because chromatic aberration is likely to occur if the second lens group G2 is driven during focusing.

It is more preferable that the endoscope optical system satisfies the following conditional equation (5)' or conditional equation (5)" in place of the above-described conditional equation (5):

$$15 < v41 - v42 < 35 \quad (5)'$$

$$20 < v41 - v42 < 25 \quad (5)''$$

$$0.2 < LD2/ih < 3.0 \quad (6)$$

where LD2 is a maximum drive amount upon focusing.

The conditional equation (6) relates to the maximum drive amount of the second lens group G2. Because the drive amount is appropriate if the value falls within the conditional equation (6), it is possible to smoothly change an observation state from normal observation to high-magnification observation. It is undesirable that the value is below a lower limit of the conditional equation (6) because the observation state largely changes with a small amount of drive. It is also undesirable that the value exceeds an upper limit of the conditional equation (6) because the entire length becomes too long.

It is more preferable that the endoscope optical system satisfies the following conditional equation (6)' or conditional equation (6)" in place of the above-described conditional equation (6):

$$0.5 < LD2/ih < 2.0 \quad (6)'$$

$$1.0 < LD2/ih < 1.4 \quad (6)''$$

$$-0.05 < PW\_G2/ih < -1 \quad (7)$$

where PW_G2 is refractive power of the second lens group.

The conditional equation (7) relates to refractive power of the second lens group. If the refractive power of the second lens group falls within the conditional equation (7), because the second lens group is disposed to have appropriate refractive power, it is possible to smoothly change the observation state from normal observation to high-magnification observation. It is undesirable that the refractive power of the second lens group is below the conditional equation (7), because the refractive power becomes too large and the observation state largely changes with a small amount of lens drive. It is also undesirable that the refractive power of the second lens group exceeds an upper limit of the conditional equation (7), because the amount of lens drive becomes long, which makes the entire length too long.

It is more preferable that the endoscope optical system satisfies the following conditional equation (7)' or conditional equation (7)" in place of the above-described conditional equation (7):

$$-0.11 < PW\_G2/ih < -0.30 \quad (7)'$$

$$-0.18 < PW\_G2/ih < -0.23 \quad (7)''$$

$$-2.0 < PW\_L01/ih < -0.1 \quad (8)$$

where PW_L01 is refractive power of the first lens L1.

The conditional equation (8) relates to the refractive power of the first lens. If the refractive power of the first lens falls within the range of the conditional equation (8), because the refractive power of the lens is appropriate, even in the optical system having an angle of view of 150 degrees or more, it is possible to apply the endoscope optical system to an endoscope without increasing the diameter of the first lens L1. It is undesirable that the refractive power of the first lens exceeds an upper limit of the conditional equation (8), because the refractive power of the first lens L1 becomes too weak, which may increase the diameter of the first lens L1. It is also undesirable that the refractive power of the first lens is below a lower limit of the conditional equation (8), because the refractive power of the first lens L1 becomes too large, the endoscope optical system becomes vulnerable to manufacturing errors and image quality is likely to degrade.

It is more preferable that the endoscope optical system satisfies the following conditional equation (8)' or conditional equation (8)" in place of the above-described conditional equation (8):

$$-1.0 < PW\_L01/ih < -0.3 \quad (8)'$$

$$-0.7 < PW\_L01/ih < -0.6 \quad (8)''$$

$$10 < v31 - v32 < 50 \quad (9)$$

where $v31$ and $v32$ are Abbe's numbers of a lens having negative refractive power and a lens having positive refractive power constituting a connected lens of the first lens group.

The conditional equation (9) is a conditional equation for the connected lens CL1 of the first lens group G1. If a difference between the Abbe's numbers falls within the range of the conditional equation (9), because the difference between the Abbe's numbers is appropriate as the connected lens, it is possible to favorably correct on-axis and off-axis chromatic aberration. It is undesirable that the difference between the Abbe's numbers exceeds an upper limit or is below a lower limit of the conditional equation (9), because the difference between the Abbe's numbers is inappropriate, which makes it difficult to correct on-axis and off-axis chromatic aberration.

It is more preferable that the endoscope optical system satisfies the following conditional equation (9)' or conditional equation (9)" in place of the above-described conditional equation (9):

$$15 < v31 - v32 < 40 \quad (9)'$$

$$20 < v31 - v32 < 35 \quad (9)''$$

$$25 < v61 - v62 < 70 \quad (10)$$

where $v61$ and $v62$ are Abbe's numbers of a lens having negative refractive power and a lens having positive refractive power constituting a connected lens CL3 of the third lens group G3.

The conditional equation (10) is a conditional equation for the connected lens of the third lens group G3, and if a difference between the Abbe's numbers falls within the range of the conditional equation (10), because the difference between the Abbe's numbers is appropriate as the connected lens, it is possible to favorably correct on-axis and off-axis chromatic aberration. It is undesirable that the difference exceeds an upper limit or is below a lower limit of the conditional equation (10), because the difference between the Abbe's numbers is inappropriate, which makes it difficult to correct the on-axis and off-axis chromatic aberration.

It is more preferable that the endoscope optical system satisfies the following conditional equation (10)' or conditional equation (10)" in place of the above-described conditional equation (10):

$$30 < v61 - v62 < 60 \quad (10)'$$

$$35 < v61 - v62 < 50 \quad (10)''$$

$$1.0 < PW\_G1/PW\_G3 < 2.0 \quad (11)$$

where PW_G1 is refractive power of the first lens group and PW_G3 is refractive power of the third lens group.

The conditional equation (11) represents a ratio of focal length of the first lens group to the third lens group G3. It is preferable that the ratio falls within the range of the conditional equation (11), because the positive refractive power can be appropriately divided between the first lens group G1 and the third lens group G3, which facilitates correction of aberration at each group. Further, it is preferable because sensitivity to manufacturing errors can be appropriately divided. It is undesirable that the ratio exceeds an upper limit or is below a lower limit of the conditional equation (11), because refractive power of any one of the lens group becomes too large, which makes it difficult to correct aberration and results in too high sensitivity to manufacturing errors.

It is more preferable that the endoscope optical system satisfies the following conditional equation (11)' or conditional equation (11)" in place of the above-described conditional equation (11):

$$1.3 < PW\_G1/PW\_G3 < 1.8 \quad (11)'$$

$$1.5 < PW\_G1/PW\_G3 < 1.6 \quad (11)''$$

$$5.0 < L\_all/ih < 20.0 \quad (12)$$

where L_all is the entire length of the endoscope optical system.

The conditional equation (12) is a conditional equation for the entire length of the endoscope optical system. If the value falls within the range of the conditional equation (12), because the entire length is appropriate, a hard length of the endoscope does not become too large, and a load is not imposed on a subject during the examination. It is undesirable that the value exceeds an upper limit of the conditional equation (12), because the hard length becomes too long, which increase the load on the subject. It is also undesirable that the value is below a lower limit of the conditional equation (12), because the entire length becomes too short, which requires to significantly increase refractive power of each group, and results in an optical system vulnerable to manufacturing errors.

It is more preferable that the endoscope optical system satisfies the following conditional equation (12)' or conditional equation (12)" in place of the above-described conditional equation (12):

$$8.0 < L\_all/ih < 15.0 \quad (12)'$$

$$11.0 < L\_all/ih < 12.5 \quad (12)''$$

It is preferable that the lenses constituting the endoscope optical system are all spherical lenses.

Because a diameter of a lens which can be adapted to the endoscope is very small, the use of a non-spherical lens or a diffraction optical element poses problems such as difficulty in manufacturing, higher costs, and degradation in performance that may be caused unless a manufacturing error is extremely small. Accordingly, in order to achieve lower costs and stable optical performance even if a manufacturing error occurs, it is preferable that all the lenses are spherical lenses.

As described above, according to this embodiment, it is possible to realize a smaller size endoscope optical system with a wide angle of view, while being capable of focusing, with appropriately corrected aberration. Further, it is possible to reduce the number of lenses constituting the endoscope optical system, reduce the entire length and reduce manufacturing costs.

EXAMPLES

Examples 1 to 3 of the endoscope optical system according to the above-described embodiment will be described with reference to FIG. 2A to FIG. 10. In lens data described in each example, r indicates a curvature radius (mm), d indicates an interval between surfaces (mm), Nd indicates a refractive index with respect to a line d, and Vd indicates an Abbe's number with respect to the line d.

Example 1

Figure 2A:
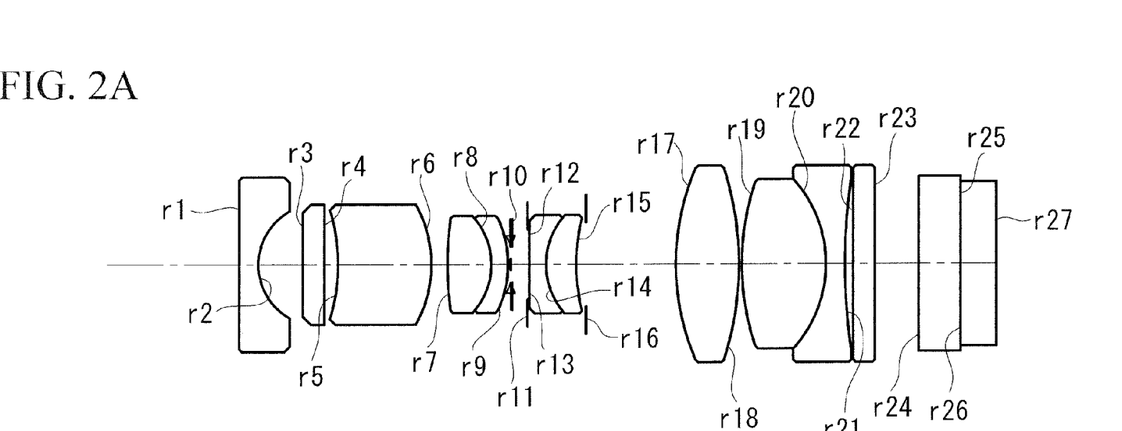
Figure 2B:
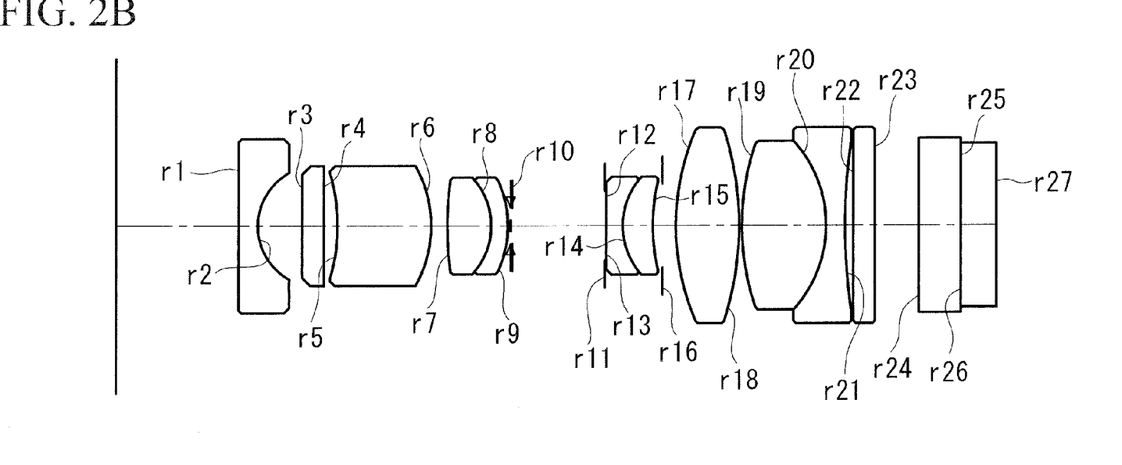
Figure 3:
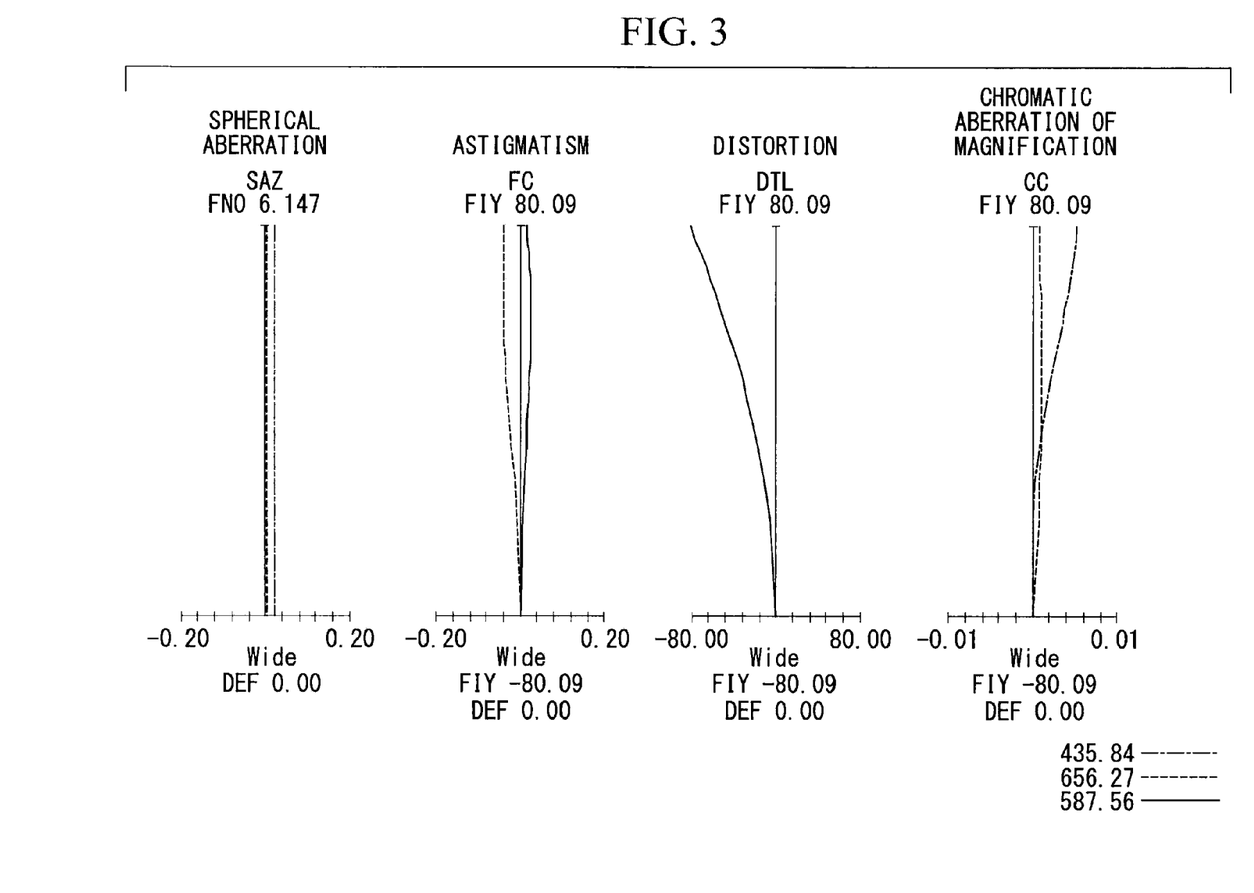
FIG. 3 shows diagrams illustrating aberration curves in the normal observation state of the endoscope optical system in FIG. 2A.
Figure 4:
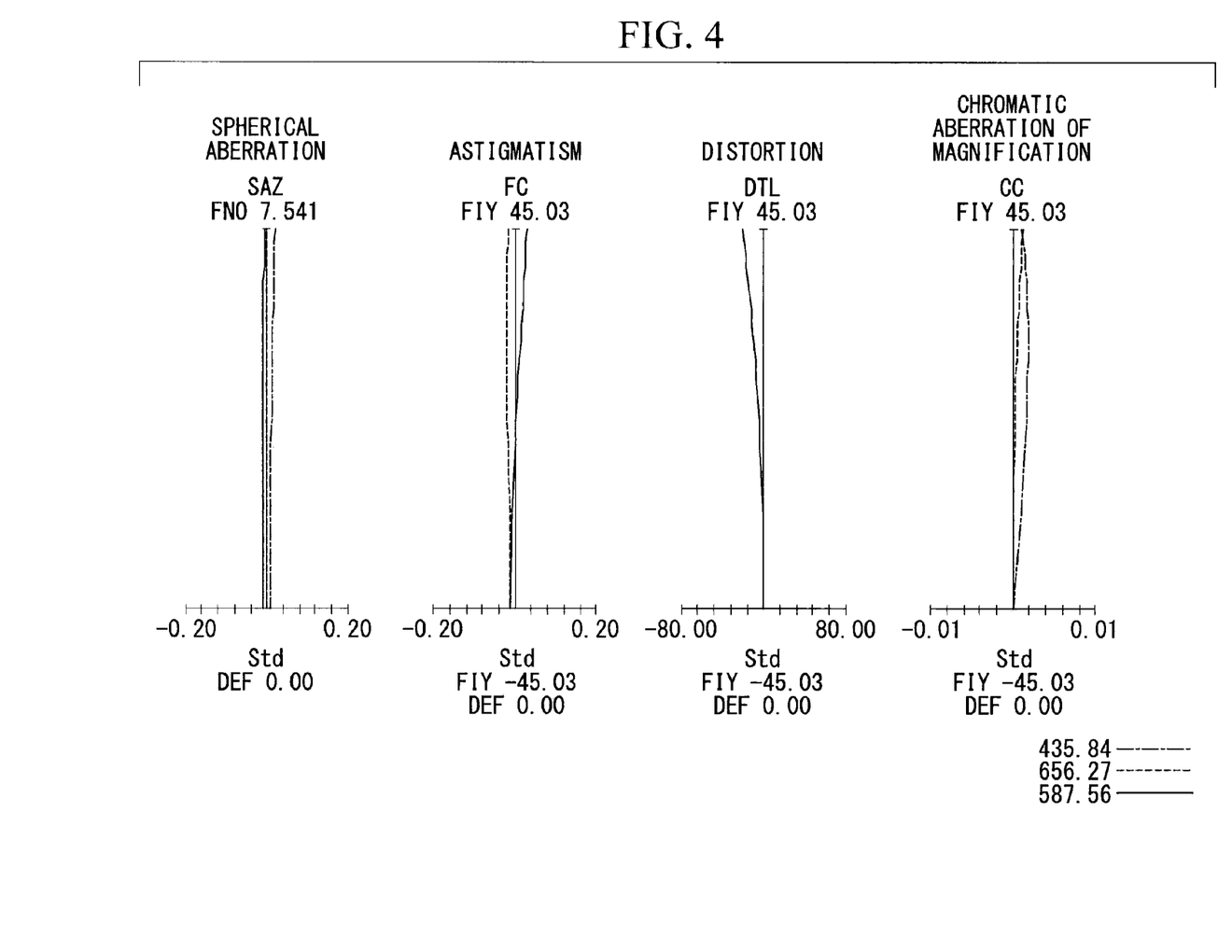
FIG. 4 shows diagrams illustrating aberration curves in the high-magnification observation state in the endoscope optical system in FIG. 2B.

FIGS. 2A and 2B illustrate a configuration of an endoscope optical system according to Example 1 of the present invention. It should be noted that FIG. 2A illustrates a normal observation state, and FIG. 2B illustrates a high-magnification observation state. Further, FIG. 3 illustrates an aberration curve in the normal observation state of the endoscope optical system according to this example, and FIG. 4 illustrates an aberration curve in the high-magnification observation state.

Lens data of the endoscope optical system according to Example 1 of the present invention will be shown below.

| Lens data | | | | |
|---|---|---|---|---|
| Surface number | r | d | Nd | vd |
| 1 | ∞ | 0.35 | 1.88300 | 40.76 |
| 2 | 1.132 | 0.80 | | |
| 3 | ∞ | 0.40 | 1.52100 | 65.12 |
| 4 | ∞ | 0.25 | | |
| 5 | −3.398 | 1.70 | 1.58144 | 40.75 |
| 6 | −2.280 | 0.30 | | |
| 7 | 6.543 | 0.80 | 1.51742 | 52.43 |
| 8 | −1.322 | 0.30 | 1.92286 | 18.90 |
| 9 | −2.049 | 0.05 | | |
| 10(S) | Diaphragm | 0.03 | | |
| 11 | ∞ | D11 | | |
| 12 | ∞ | 0.03 | | |
| 13 | ∞ | 0.30 | 1.77250 | 49.60 |
| 14 | 1.354 | 0.55 | 1.72825 | 28.46 |
| 15 | 3.521 | 0.18 | | |
| 16 | ∞ | D16 | | |
| 17 | 4.480 | 1.15 | 1.81600 | 46.62 |
| 18 | −5.772 | 0.05 | | |
| 19 | 4.703 | 1.53 | 1.61800 | 63.33 |
| 20 | −2.320 | 0.35 | 1.92286 | 18.90 |
| 21 | 10.721 | 0.15 | | |
| 22 | ∞ | 0.40 | 1.52300 | 58.59 |
| 23 | ∞ | 0.80 | | |

-continued

| Lens data | | | | |
|---|---|---|---|---|
| 24 | ∞ | 0.75 | 1.51633 | 64.14 |
| 25 | ∞ | 0.01 | 1.51300 | 64.01 |
| 26 | ∞ | 0.65 | 1.50510 | 63.26 |
| 27 | | | | |

| Various data | Normal observation | High-magnification observation | |
|---|---|---|---|
| Focal length | 1.14 | 1.40 | |
| FNO. | 6.15 | 7.54 | |
| Angle of view2ω | 160.29 | 90.20 | |
| D11 | 0.28 | 1.68 | 1.68 |
| D16 | 1.64 | 0.24 | 0.24 |
| Entire length 13.09 mm | | | |

| Focal length of each group | | |
|---|---|---|
| First lens group | Second lens group | Third lens group |
| 1.93 | −4.14 | 3.08 |

Example 2

Figure 5A:
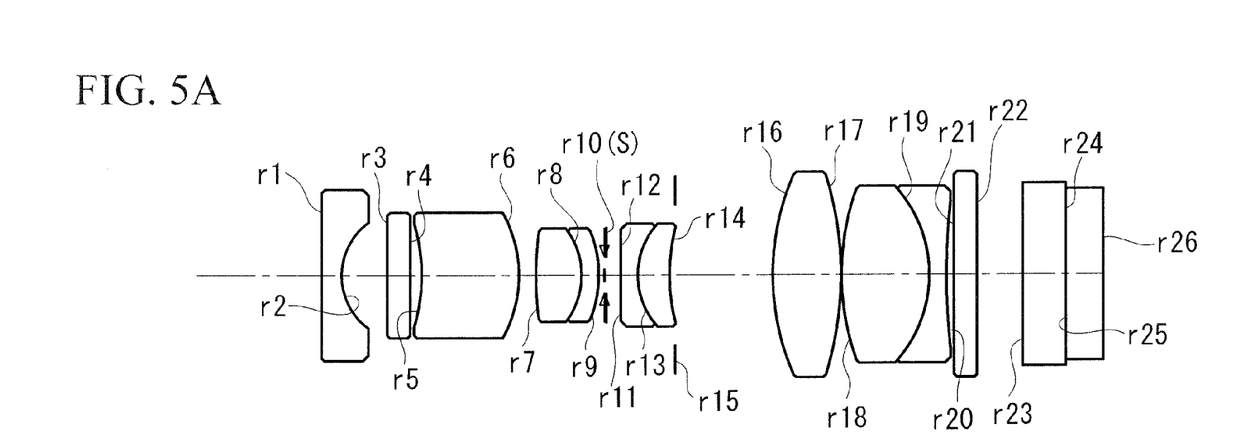
Figure 5B:
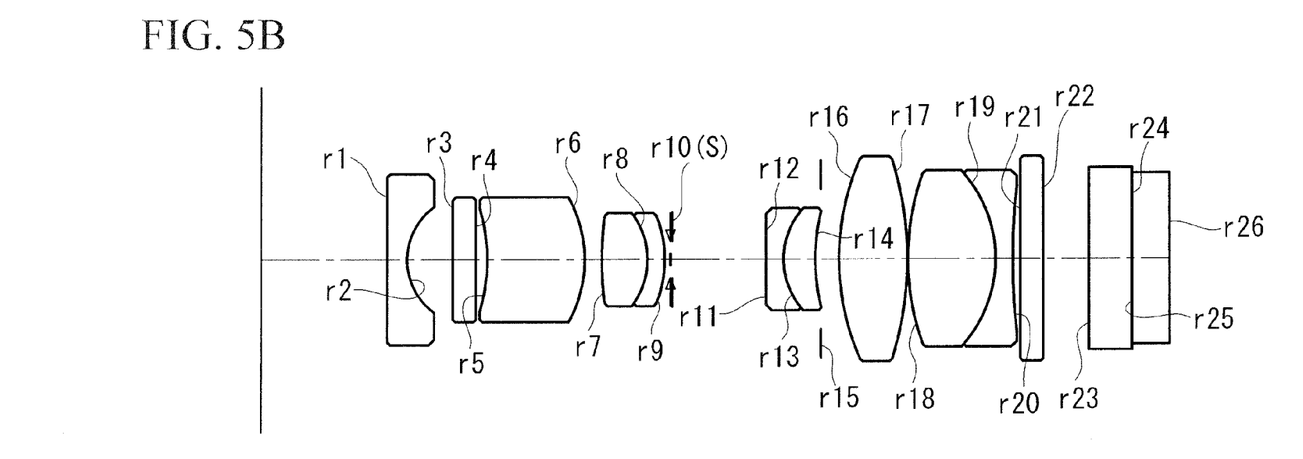
Figure 6:
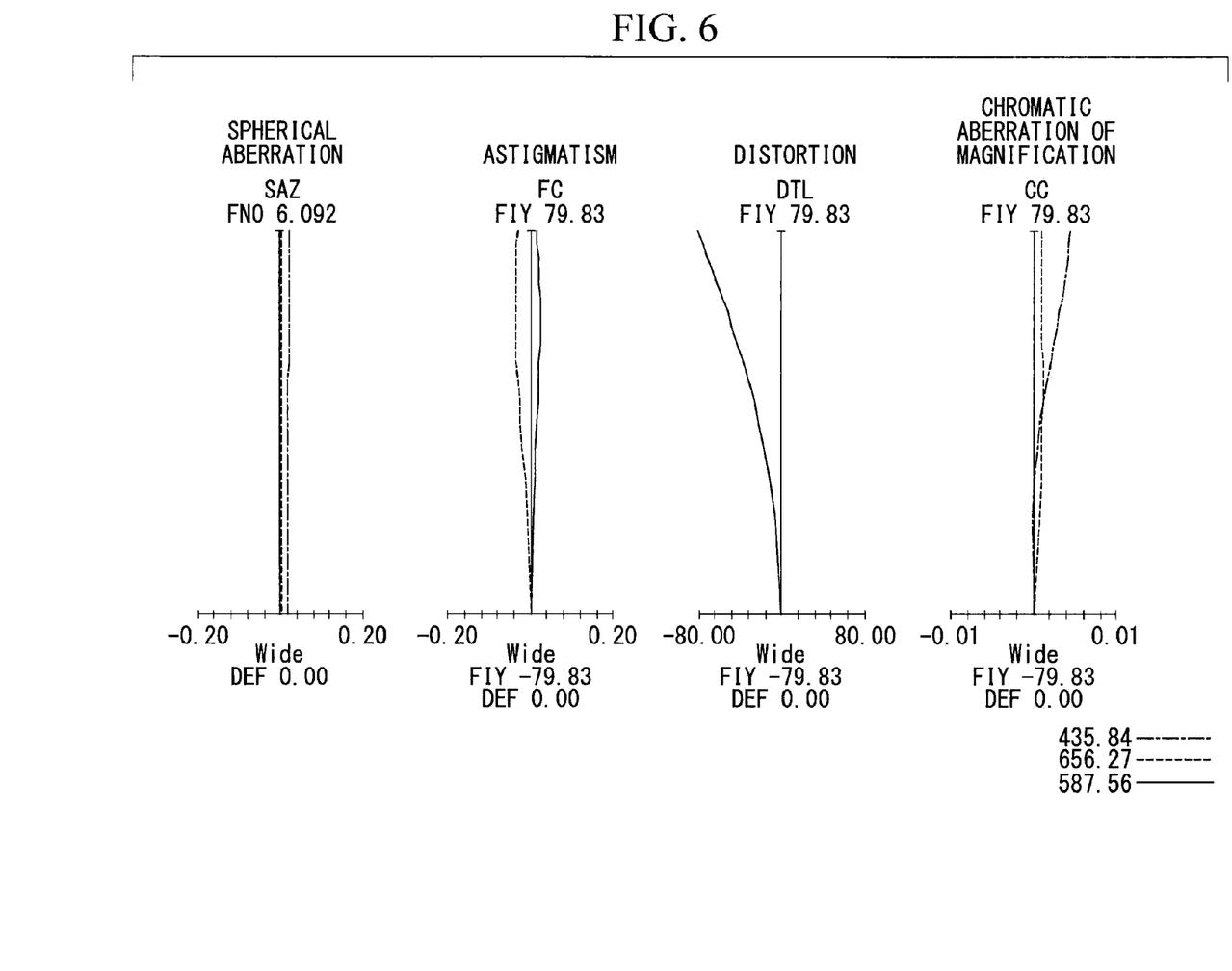
FIG. 6 shows diagrams illustrating aberration curves in the normal observation state of the endoscope optical system in FIG. 5A.
Figure 7:
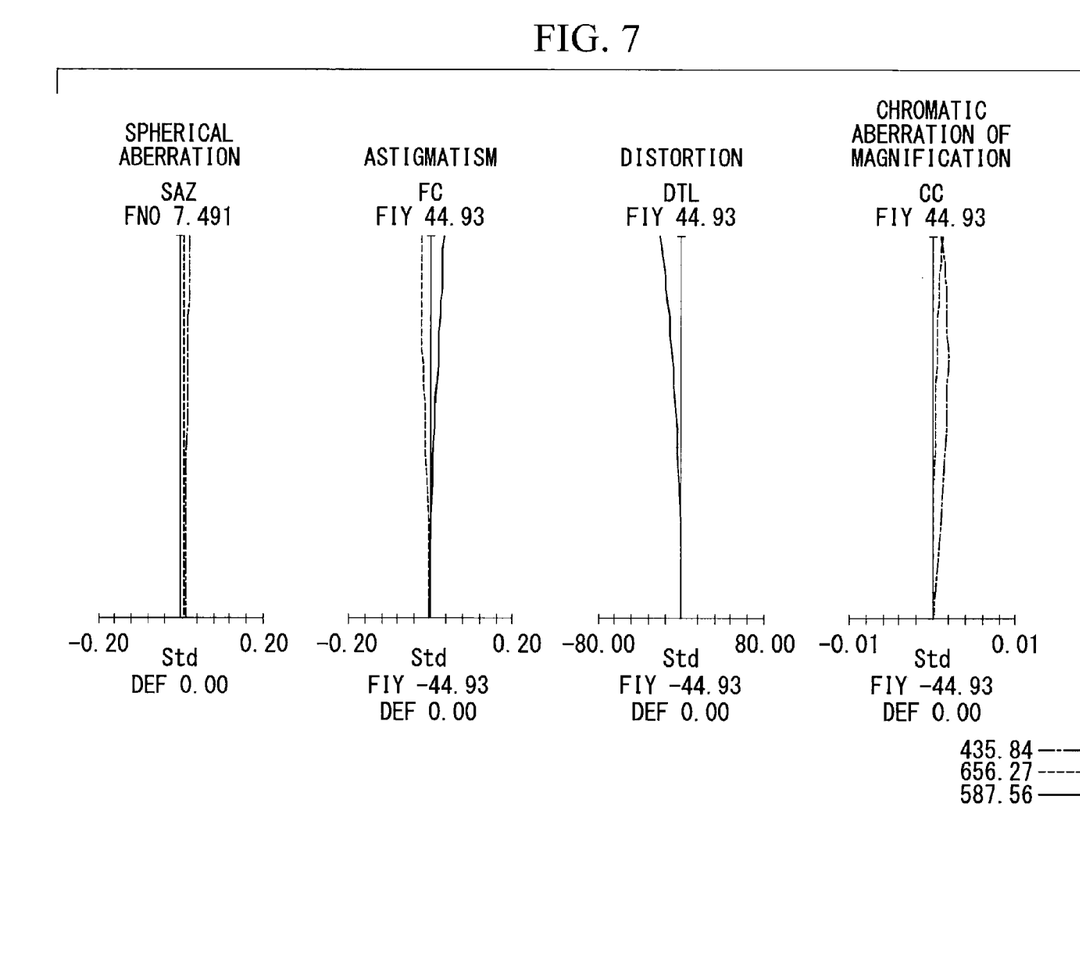
FIG. 7 shows diagrams illustrating aberration curves in the high-magnification observation state of the endoscope optical system in FIG. 5B.

FIGS. 5A and 5B illustrate a configuration of an endoscope optical system according to Example 2 of the present invention. It should be noted that FIG. 5A illustrates a normal observation state, and FIG. 5B illustrates a high-magnification observation state. Further, FIG. 6 illustrates an aberration curve of the normal observation state of the endoscope optical system according to this example, and FIG. 7 illustrates an aberration curve of the high-magnification observation state.

Lens data of the endoscope optical system according to Example 2 of the present invention will be shown below.

| Lens data | | | | |
|---|---|---|---|---|
| Surface number | r | d | Nd | vd |
| 1 | ∞ | 0.35 | 1.88300 | 40.76 |
| 2 | 1.143 | 0.80 | | |
| 3 | ∞ | 0.40 | 1.52100 | 65.12 |
| 4 | ∞ | 0.20 | | |
| 5 | −3.168 | 1.70 | 1.58144 | 40.75 |
| 6 | −2.275 | 0.30 | | |
| 7 | 5.612 | 0.80 | 1.51742 | 52.43 |
| 8 | −1.347 | 0.30 | 1.92286 | 18.90 |
| 9 | −2.088 | 0.10 | | |
| 10(S) | Diaphragm | 0.03 | | |
| 11 | ∞ | 0.26 | | |
| 12 | ∞ | 0.30 | 1.77250 | 49.60 |
| 13 | 1.355 | 0.55 | 1.72825 | 28.46 |
| 14 | 3.429 | 0.10 | | |
| 15 | ∞ | 1.70 | | |
| 16 | 4.388 | 1.20 | 1.81600 | 46.62 |
| 17 | −5.888 | 0.01 | | |
| 18 | 4.441 | 1.53 | 1.60300 | 65.44 |
| 19 | −2.320 | 0.30 | 1.92286 | 18.90 |
| 20 | 11.964 | 0.13 | | |
| 21 | ∞ | 0.40 | 1.52300 | 58.59 |
| 22 | ∞ | 0.80 | | |

-continued

| Lens data | | | | |
|---|---|---|---|---|
| 23 | ∞ | 0.75 | 1.51633 | 64.14 |
| 24 | ∞ | 0.01 | 1.51300 | 64.01 |
| 25 | ∞ | 0.65 | 1.50510 | 63.26 |
| 26 | | | | |

| Various data | Normal observation | High-magnification observation |
|---|---|---|
| Focal length | 1.14 | 1.40 |
| FNO. | 6.09 | 7.49 |
| Angle of view2ω | 159.85 | 90.00 |
| Entire length 12.96 mm | | |

| Focal length of each group | | |
|---|---|---|
| First lens group | Second lens group | Third lens group |
| 1.92 | −4.05 | 3.03 |

Example 3

Figure 8A:
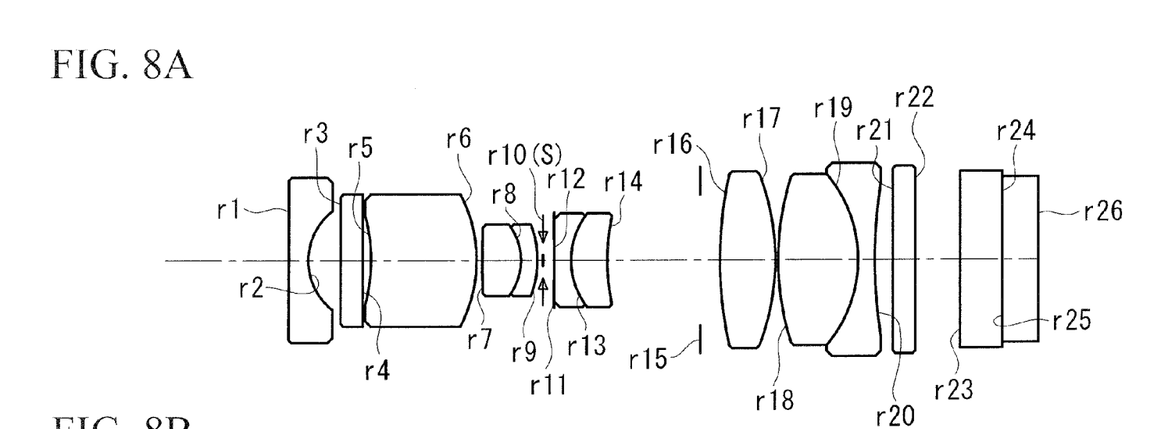
Figure 8B:
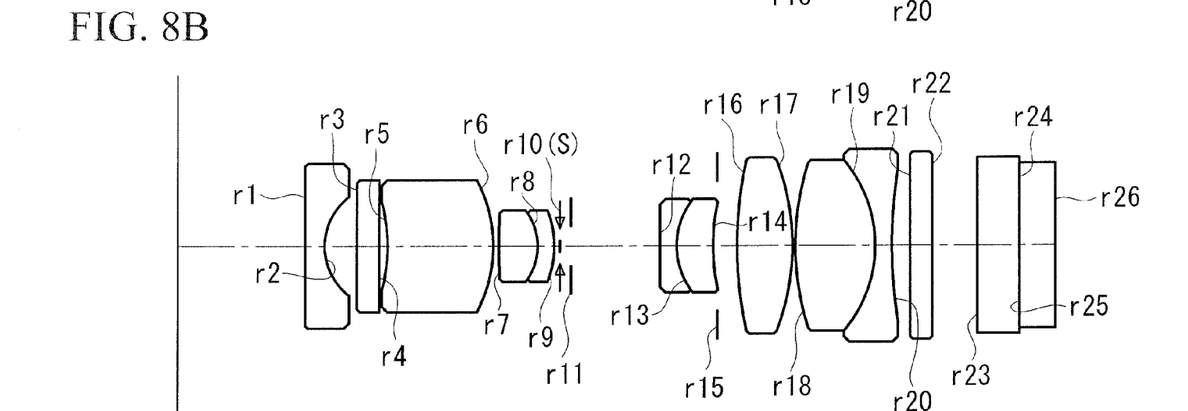
Figure 9:
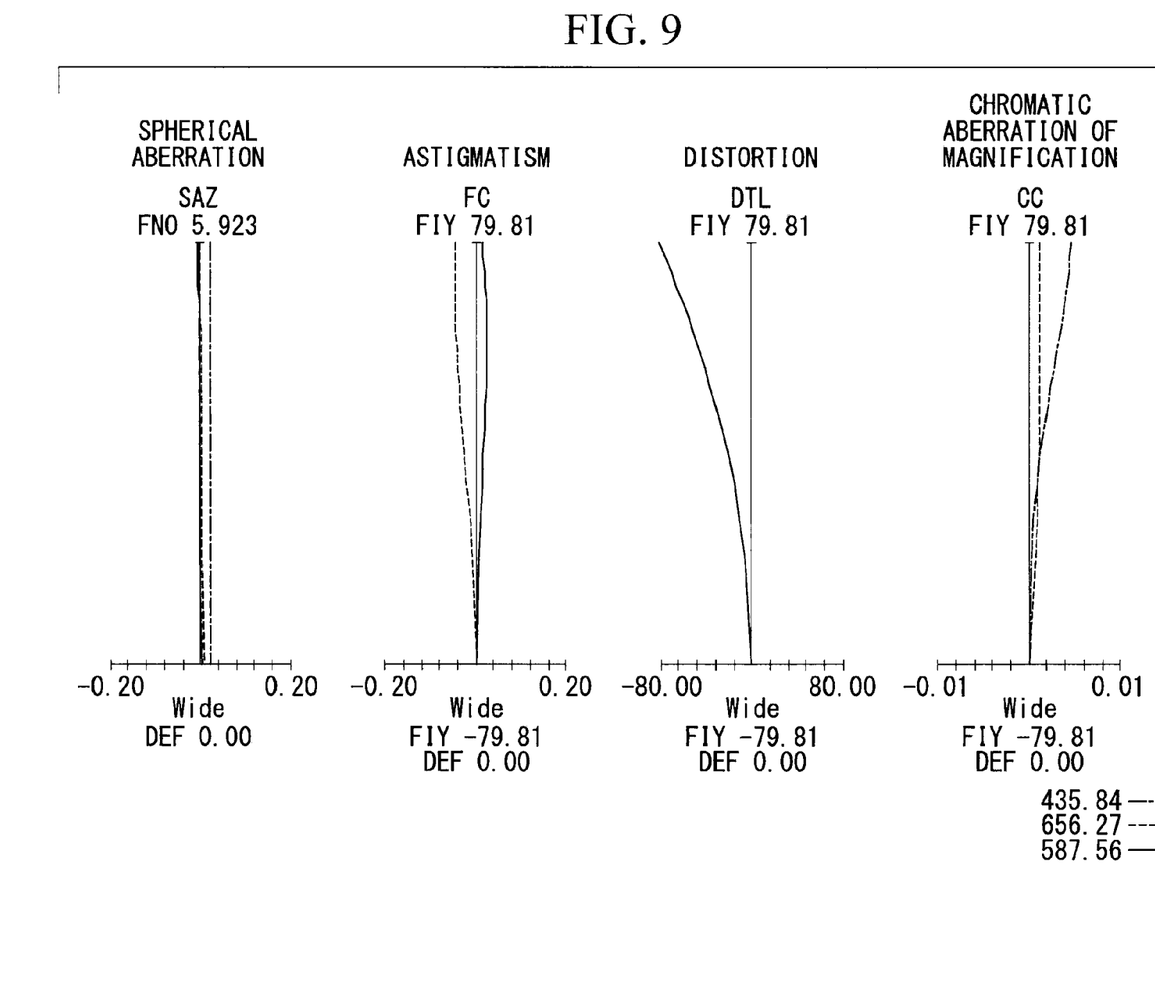
FIG. 9 shows diagrams illustrating aberration curves in the normal observation state of the endoscope optical system in FIG. 8A.
Figure 10:
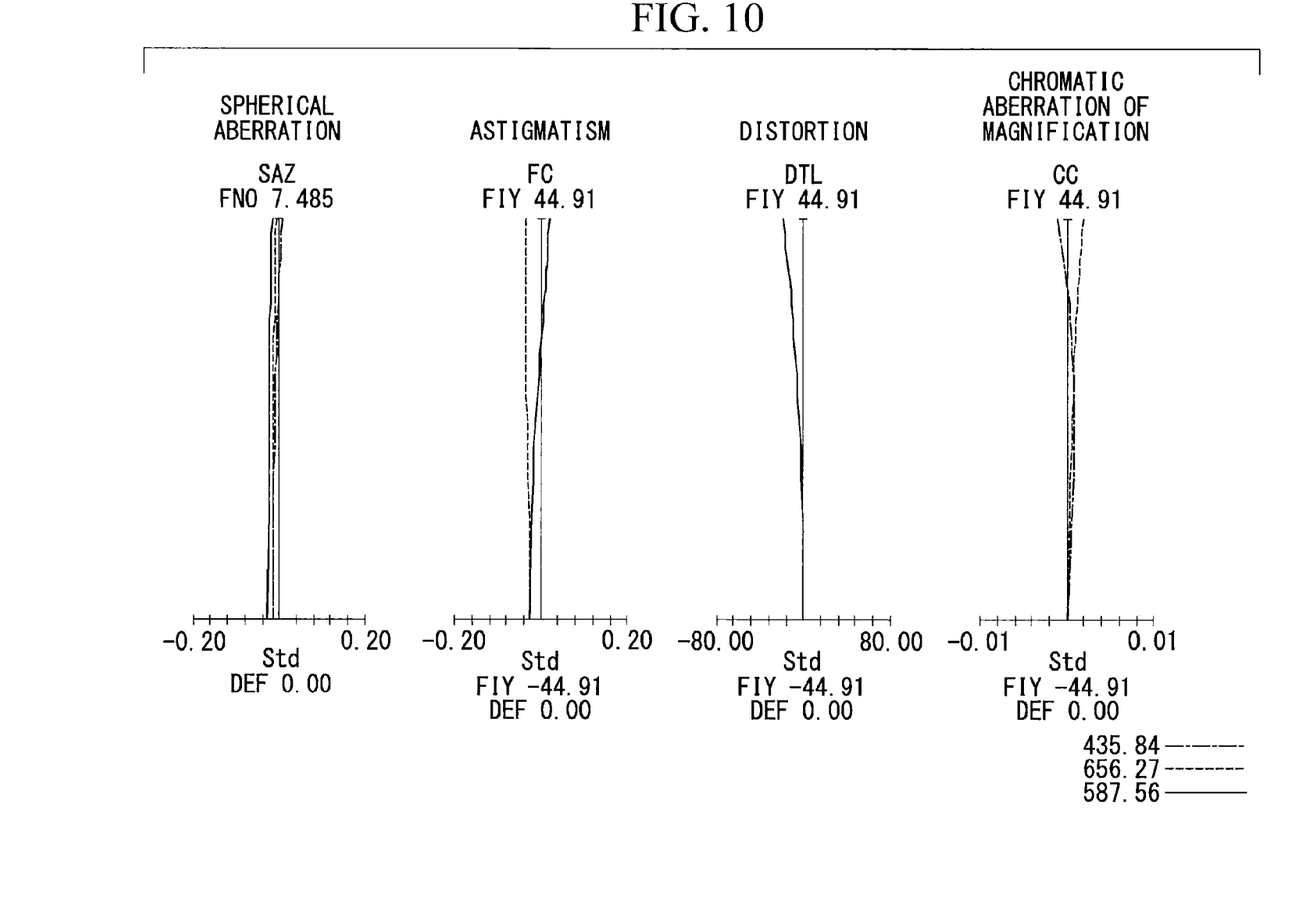
FIG. 10 shows diagrams illustrating aberration curves in the high-magnification observation state of the endoscope optical system in FIG. 8B.

FIGS. 8A and 8B illustrate a configuration of an endoscope optical system according to Example 3 of the present invention. It should be noted that FIG. 8A illustrates a normal observation state, and FIG. 8B illustrates a high-magnification observation state. Further, FIG. 9 illustrates an aberration curve of the normal observation state of the endoscope optical system according to this example, and FIG. 10 illustrates an aberration curve of the high-magnification observation state.

Lens data of the endoscope optical system according to Example 3 of the present invention will be shown below.

| Lens data | | | | |
|---|---|---|---|---|
| Surface number | r | d | Nd | vd |
| 1 | ∞ | 0.35 | 1.88300 | 40.76 |
| 2 | 1.144 | 0.58 | | |
| 3 | ∞ | 0.40 | 1.52100 | 65.12 |
| 4 | ∞ | 0.15 | | |
| 5 | −3.090 | 1.90 | 1.58144 | 40.75 |
| 6 | −2.598 | 0.10 | | |
| 7 | 12.217 | 0.70 | 1.58144 | 40.75 |
| 8 | −1.073 | 0.30 | 1.92286 | 18.90 |
| 9 | −1.786 | 0.10 | | |
| 10(S) | Diaphragm | 0.20 | | |
| 11 | ∞ | D11 | | |
| 12 | ∞ | 0.30 | 1.77250 | 49.60 |
| 13 | 1.398 | 0.65 | 1.72825 | 28.46 |
| 14 | 3.845 | D14 | | |
| 15 | ∞ | 0.35 | | |
| 16 | 7.303 | 1.00 | 1.83481 | 42.71 |
| 17 | −4.300 | 0.05 | | |
| 18 | 4.950 | 1.45 | 1.69680 | 55.53 |
| 19 | −2.400 | 0.30 | 1.92286 | 18.90 |
| 20 | 8.739 | 0.33 | | |
| 21 | ∞ | 0.40 | 1.52300 | 58.59 |
| 22 | ∞ | 0.80 | | |
| 23 | ∞ | 0.75 | 1.51633 | 64.14 |
| 24 | ∞ | 0.01 | 1.51300 | 64.01 |
| 25 | ∞ | 0.65 | 1.50510 | 63.26 |
| 26 | | | | |

-continued

| Lens data | | |
|---|---|---|
| Various data | Normal observation | High-magnification observation |
| Focal length | 1.11 | 1.40 |
| FNO. | 5.92 | 7.48 |
| Angle of view2ω | 159.85 | 90.00 |
| D11 | 0.01 | 1.61 |
| D14 | 1.68 | 0.08 |
| Entire length 12.80 mm | | |

| Focal length of each group | | |
|---|---|---|
| First lens group | Second lens group | Third lens group |
| 2.04 | −4.48 | 3.12 |

It should be noted that values of the above-described conditional equations (1) to (12) in the configurations in the above-described Examples 1 to 3 are shown in Table 1.

TABLE 1

| NUMBER | CONDITIONAL EQUATION | EXAMPLE 1 | EXAMPLE 2 | EXAMPLE 3 |
|---|---|---|---|---|
| 1 | H(76) * (1 − nd01)/r2 | −0.635 | −0.825 | −0.785 |
| 2 | (r1 + r2)/(r1 − r2) | 1.000 | 1.000 | 1.000 |
| 3 | D_L02/ih | 1.480 | 1.480 | 1.654 |
| 4 | nd01 | 1.888 | 1.888 | 1.888 |
| 5 | ν41 − ν42 | 21.140 | 21.140 | 21.140 |
| 6 | LD2/ih | 1.218 | 1.200 | 1.392 |
| 7 | PW_G2/ih | −0.210 | −0.215 | −0.194 |
| 8 | PW_L01/ih | −0.683 | −0.676 | −0.675 |
| 9 | ν31 − ν32 | 33.530 | 33.530 | 21.850 |
| 10 | ν61 − ν62 | 44.430 | 46.540 | 36.360 |
| 11 | PW_G1/PW_G3 | 1.598 | 1.581 | 1.527 |
| 12 | L_all/ih | 12.010 | 11.898 | 11.755 |

On the basis of the embodiment described above, inventions as follows are derived.

One aspect of the present invention is an endoscope optical system including a first lens group having positive refractive power, an aperture diaphragm, a second lens group having negative refractive power and a third lens group having positive refractive power, in this order from an object side toward an image side, focusing being performed by the second lens group moving along an optical axis, the first lens group including a first lens having negative refractive power and a second lens having positive refractive power, in this order from the object side, and the endoscope optical system satisfying the following conditional equations:

$$-5.0 < H(76)*(1-nd01)/r2 < -0.2 \quad (1)$$

$$0.5 < (r1+r2)/(r1-r2) < 1.2 \quad (2)$$

where H(76) is a height at which a principal ray having an incidence angle of view of 76 degrees during normal observation passes through a surface on the image side of the first lens, nd01 is a refractive index of the first lens with respect to a line d, and r1 and r2 are respectively curvature radii of a surface on the object side and the surface on the image side of the first lens.

According to the above-described aspect, by providing the first lens group having positive refractive power (hereinafter, simply referred to as "positive"), the aperture diaphragm, the second lens group having negative refractive power (hereinafter, simply referred to as "negative") and the third positive lens group, it is possible to realize a smaller size endoscope optical system, while being capable of focusing, which has a wide angle of view with appropriately corrected aberration. Further, it is possible to reduce the number of lenses constituting the endoscope optical system, so that it is possible to reduce the entire length and reduce manufacturing costs.

In the above-described invention, it is preferable that the following conditional equation is satisfied:

$$0.5 < D\_L02/ih < 5.0 \quad (3)$$

where D_L02 is a thickness of the second lens on the optical axis, and ih is a maximum image height.

With this configuration, it is possible to maintain an appropriate thickness of the second lens and maintain an appropriate entire length of the endoscope optical system while favorably correcting off-axis aberration such as astigmatism.

In the above-described invention, it is preferable that the following conditional equation is satisfied:

$$1.65 < nd01 < 2.4 \quad (4)$$

where nd01 is a refractive index of the first lens with respect to a line d.

With this configuration, because the refractive index of the first lens can be maintained appropriately, it is possible to obtain appropriate negative refractive power without extremely increasing curvatures of the first lens and the second lens on the object side.

In the above-described aspect, it is preferable that the second lens group is composed of only a connected lens of a lens having negative refractive power and a lens having positive refractive power, and the endoscope optical system satisfies the following conditional equation:

$$10 < \nu 41 - \nu 42 < 45 \quad (5)$$

where ν41 and ν42 are respectively Abbe's numbers of the lens having the negative refractive power and the lens having the positive refractive power of the second lens group.

With this configuration, it is possible to set appropriate values for the Abbe's numbers of the second lens group, so that extreme chromatic aberration does not occur even if the second lens is driven during focusing.

In the above-described aspect, the second lens group preferably satisfies the following conditional equation:

$$0.2 < LD2/ih < 3.0 \quad (6)$$

where LD2 is a maximum drive amount upon focusing.

With this configuration, it is possible to maintain an appropriate maximum drive amount of the second lens group, so that it is possible to smoothly change an observation state from normal observation to high-magnification observation.

In the above-described aspect, it is preferable that the following conditional equation is satisfied:

$$-0.05 < PW\_G2/ih < -1 \quad (7)$$

where PW_G2 is a focal distance of the second lens.

With this configuration, because it is possible to set an appropriate value for the refractive power of the second lens group, it is possible to smoothly change the observation state from normal observation to high-magnification observation.

In the above-described aspect, it is preferable that the following conditional equation is satisfied:

$$-2.0 < PW\_L01/ih < -0.1 \quad (8)$$

where PW_L01 is refractive power of the first lens.

With this configuration, because it is possible to set an appropriate value for the refractive power of the first lens, the diameter of the first lens will not become extremely large while a wide angle of view is realized.

In the above-described aspect, it is preferable that the first lens group is composed of a first lens having negative refractive power, a second lens having positive refractive power and a connected lens of a lens having positive refractive power and a lens having negative refractive power, in this order from the object side toward the image side and satisfies the following conditional equation:

$$10<\nu 31-\nu 32<50 \quad (9)$$

where ν31 and ν32 are Abbe's numbers of the lens having negative refractive power and the lens having positive refractive power constituting the connected lens of the first lens group.

With this configuration, because it is possible to set appropriate Abbe's numbers for the connected lens of the lens having positive refractive power and the lens having negative refractive power of the first lens group, it is possible to favorably correct on-axis and off-axis chromatic aberration.

In the above-described aspect, it is preferable that the third lens group is composed of a lens having positive refractive power, and a connected lens of a lens having positive refractive power and a lens having negative refractive power, in this order from the object side toward the image side, and satisfies the following conditional equation:

$$25<\nu 61-\nu 62<70 \quad (10)$$

where ν61 and ν62 indicate Abbe's numbers of the lens having negative refractive power and the lens having positive refractive power constituting the connected lens of the third lens group.

With this configuration, because it is possible to set appropriate Abbe's numbers for the connected lens of the lens having positive refractive power and the lens having negative refractive power of the third lens group, it is possible to favorably correct on-axis and off-axis chromatic aberration.

In the above-described aspect, it is preferable that the following conditional equation is satisfied:

$$1.0<PW\_G1/PW\_G3<2.0 \quad (11)$$

where PW_G1 is refractive power of the first lens group, and PW_G3 is refractive power of the third lens group.

With this configuration, because it is possible to appropriately divide the positive refractive power between the first lens group and the third lens group, it is possible to easily correct aberration of each lens group and appropriately divide sensitivity to a manufacturing error.

In the above-described aspect, it is preferable that the following conditional equation is satisfied:

$$5.0<L\_all/ih<20.0 \quad (12)$$

where L_all is the entire length of the optical system.

With this configuration, because it is possible to set an appropriate length for the entire length of the endoscope optical system, a hard length of the endoscope does not become too large, so that it is possible to reduce a load on a subject during examination.

In the above-described aspect, it is preferable that the lenses constituting the optical system are all spherical lenses.

With this configuration, it is possible to reduce cost and maintain stable optical performance even when a manufacturing error occurs.

ADVANTAGEOUS EFFECTS OF INVENTION

The present invention provides an advantageous effect that it is possible to realize a smaller size endoscope optical system with a wide angle of view with appropriately corrected aberration.

REFERENCE SIGNS LIST

G1 First lens group
G2 Second lens group
G3 Third lens group
L1 First lens
L2 Second lens
L3 Third lens
L4 Fourth lens
L5 Fifth lens
L6 Sixth lens
L7 Seventh lens
L8 Eighth lens
L9 Ninth lens
CL1 Connected lens
CL2 Connected lens
CL3 Connected lens
S Aperture diaphragm
F1 Parallel flat plate
F2 Parallel flat plate
F3 Parallel flat plate
CG Cover glass

The invention claimed is:

1. An endoscope optical system consisting of a first lens group having positive refractive power, an aperture diaphragm, a second lens group having negative refractive power, and a third lens group having positive refractive power, in this order from an object side to an image side, the second lens group moving along an optical axis to perform focusing, and the first lens group comprising a first lens having negative refractive power and a second lens having positive refractive power, in this order from the object side and satisfying the following conditional equations:

$$-5.0<H(76)*(1-nd01)/r2<-0.2 \quad (1)$$

$$0.5<(r1+r2)/(r1-r2)<1.2 \quad (2)$$

where H(76) is a height at which a principal ray of an incidence angle of view of 76 degrees during normal observation transmits through a surface on the image side of the first lens, nd01 is a refractive index of the first lens with respect to a line d, and r1 and r2 are respectively curvature radii of a surface on the object side and the surface on the image side of the first lens.

2. The endoscope optical system according to claim 1, satisfying the following conditional equation:

$$0.5<D\_L02/ih<5.0 \quad (3)$$

where D_L02 is a thickness of the second lens on the optical axis, and ih is a maximum image height.

3. The endoscope optical system according to claim 1, satisfying the following conditional equation:

$$1.65<nd01<2.4 \quad (4)$$

where nd01 is a refractive index of the first lens with respect to the line d.

4. The endoscope optical system according to claim 1, wherein the second lens group is composed of only a connected lens of a lens having negative refractive power and a lens having positive refractive power, and the endoscope optical system satisfies the following conditional equation:

$$10<\nu 41-\nu 42<45 \quad (5)$$

where ν41 and ν42 are respectively Abbe's numbers of the lens having negative refractive power and the lens having positive refractive power of the second lens group.

5. The endoscope optical system according to claim 4, wherein the second lens group satisfies the following conditional equation:

$$0.2 < LD2/ih < 3.0 \tag{6}$$

where LD2 is a maximum drive amount upon focusing.

6. The endoscope optical system according to claim 4, satisfying the following conditional equation:

$$-0.05 < PW\_G2/ih < -1 \tag{7}$$

where PW_G2 is refractive power of the second lens group.

7. The endoscope optical system according to claim 4, satisfying the following conditional equation:

$$-2.0 < PW\_L01/ih < -0.1 \tag{8}$$

where PW_L01 is refractive power of the first lens.

8. The endoscope optical system according to claim 4, wherein the first lens group is composed of a first lens having negative refractive power, a second lens having positive refractive power, and a connected lens of a lens having positive refractive power and a lens having negative refractive power, in this order from the object side toward the image side, and the endoscope optical system satisfies the following conditional equation:

$$10 < \nu31 - \nu32 < 50 \tag{9}$$

where ν31 and ν32 are Abbe's numbers of the lens having negative refractive power and the lens having positive refractive power constituting the connected lens of the first lens group.

9. The endoscope optical system according to claim 4, wherein the third lens group is composed of a lens having positive refractive power and a connected lens of a lens having positive refractive power and a lens having negative refractive power, and the endoscope optical system satisfies the following conditional equation:

$$25 < \nu61 - \nu62 < 70 \tag{10}$$

where ν61 and ν62 are Abbe's numbers of the lens having negative refractive power and the lens having positive refractive power constituting the connected lens of the third lens group.

10. The endoscope optical system according to claim 4, satisfying the following conditional equation:

$$1.0 < PW\_G1/PW\_G3 < 2.0 \tag{11}$$

where PW_G1 is refractive power of the first lens group, and PW_G3 is refractive power of the third lens group.

11. The endoscope optical system according to claim 4, satisfying the following conditional equation:

$$5.0 < L\_all/ih < 20.0 \tag{12}$$

where L_all is an entire length of the endoscope optical system.

* * * * *